(12) United States Patent
Nie et al.

(10) Patent No.: US 6,468,808 B1
(45) Date of Patent: Oct. 22, 2002

(54) WATER-SOLUBLE LUMINESCENT QUANTUM DOTS AND BIOMOLECULAR CONJUGATES THEREOF AND RELATED COMPOSITIONS AND METHOD OF USE

(75) Inventors: Shuming Nie; Warren C. W. Chan, both of Bloomington, IN (US); Steven R. Emory, Los Alamos, NM (US)

(73) Assignee: Advanced Research and Technology Institute, Inc., Indianapolis, IN (US)

( * ) Notice: Subject to any disclaimer, the term of this patent is extended or adjusted under 35 U.S.C. 154(b) by 0 days.

(21) Appl. No.: 09/405,653

(22) Filed: Sep. 24, 1999

Related U.S. Application Data

(60) Provisional application No. 60/131,987, filed on Apr. 30, 1999, and provisional application No. 60/101,748, filed on Sep. 24, 1998.

(51) Int. Cl.[7] ..................... G01N 33/551; G01N 33/553
(52) U.S. Cl. .......................... 436/524; 257/40; 257/64; 257/200; 257/164; 257/613; 257/642; 420/528; 420/555; 420/576; 420/577; 430/56; 430/60; 436/525; 428/402; 428/403; 435/6
(58) Field of Search ................... 430/56, 60; 420/528, 420/555, 576, 577; 257/64, 40, 200, 613, 164, 642; 436/524, 525; 428/402, 403; 435/6

(56) References Cited

U.S. PATENT DOCUMENTS

| | | |
|---|---|---|
| 3,996,345 A | 12/1976 | Ullman et al. |
| 4,637,988 A | 1/1987 | Hinshaw et al. |
| 4,777,128 A | 10/1988 | Lippa |
| 5,248,772 A | 9/1993 | Siiman et al. |
| 5,319,209 A | 6/1994 | Miyakawa et al. |
| 5,389,377 A | 2/1995 | Chagnon et al. |
| 5,441,746 A | 8/1995 | Chagnon |
| 5,505,928 A * | 4/1996 | Alivisatos et al. .......... 423/299 |
| 5,674,698 A | 10/1997 | Zarling et al. |
| 5,751,018 A * | 5/1998 | Alivisatos et al. ............ 257/64 |
| 5,990,479 A * | 11/1999 | Weiss et al. ................. 250/307 |
| 6,251,303 B1 | 6/2001 | Bawendi et al. |

FOREIGN PATENT DOCUMENTS

| | | |
|---|---|---|
| GB | 2 342 651 | 4/2000 |
| WO | WO 91/09678 | 7/1991 |
| WO | WO 93/15117 | 8/1993 |
| WO | WO 93/26019 | 12/1993 |
| WO | WO 98/04740 | 2/1998 |
| WO | WO 00/17656 | 3/2000 |

OTHER PUBLICATIONS

Lawless et al. (1995). Bifunctional capping of CdS nanoparticles and bridging to TiO2. J. Phys. Chem. 99:10329–10335.*
Hines et al. (1996). Synthesis and characterization of strongly luminescing ZnS–capped CdSe nanocrystals. J. Phys. Chem. 100:468–471.*
Matsumoto et al. (1996). Preparation of nonodisperse CdS nanocrystals by size selective photocorrosion. J. Phys. Chem. 100:13781–13785.*
Danek et al. (1996). Synthesis of luminescent thin–film CdSe/ZnSe quantum dot composites using CdSe quantum dots passivated with an overlayer of ZnSe. Chem. Mat. 8:173–180.*
Dabbousi et al. (1997). (CdSe)ZnS core–shell quantum dots: synthesis and characterization of a size series of highly luminescent nanocrystallites. J. pHys Chem. B. 101:9463–9475.*
Murray et al. (1993). Synthesis and characterization of nearly monodisperse CdE (E=S, Se, Te) semiconductor nanocrystallites. J. Am. Chem. Soc. 115(19):8706–8715.*
Norris et al. (1996). Measurement and assignment of the size–dependent optical spectrum in CdSe quantum dots. Phys. Rev. B. 53(24):16338–16346.*
Norris et al. (1996). Size dependence of exciton fine structure in CdSe quantum dots. Phys. Rev. B. 53(24):16347–16354.*
Covin et al. (1994). Light–emitting diodes made from cadmium selenide nanocrystals and a semiconducting polymer. Nature. 370:354–357.*
Dabbousi et al. (1995). Electroluminescence from CdSe quantum–dot/polymer composites. Appl. Phys. Lett. 66(11):1316–1318.*
Alivisatos (1996). Perspective on the physical chemistry of semiconductor nanocrystals. J. Phys. Chem. 100(31):13226–13239.*
Nirmal et al. (1996). Fluorescence intermittency in single cadmium selenide nnocrystals. Nature. 383:802–804.*
Alivisatos et al., "Organization of Nanocrystal Molecules Using DNA," *Nature,* 382, 609–611 (1996).
Bruchez et al., "Semiconductor Nanocrystals as Fluoredcent Probes for Biology," *Cytometry, Supp. 9,* 26(1998).
Coffer et al., "Characterization of Quantum–Confined CdD Nanocrystallites Stablized by Deoxyribonucleic Acid (DNA)," *Nanotechnol.,* 3, 69–76 (1992).
Jacoby, "Quantum Dots Meet Biomolecules," *C&E News,* 9/28, 8 (,819,898,8).
Kagan et al., "Electronic Energy Transfer in CdSe Quantum Dot Solids," *Phys. Rev. Lett.,* 76, 1577–1580 (1996).
Kuno et al., "The Band Edge Luminescence of Surface Modified CdSe Nanocrystalline: Probing the Luminescing State," *J. Chem. Phys.,* 106, 9869–9882 (1997).
Liz–Marzan et al., "Synthesis of Nanosized Gold–Silica Core–Shell Particles," *Langmuir,* 12, 4329–4335 (1996).

(List continued on next page.)

Primary Examiner—Christopher L. Chin
(74) Attorney, Agent, or Firm—Leydig, Voit & Mayer, Ltd.

(57) ABSTRACT

The present invention provides a water-soluble luminescent quantum dot, a biomolecular conjugate thereof and a composition comprising such a quantum dot or conjugate. Additionally, the present invention provides a method of obtaining a luminescent quantum dot, a method of making a biomolecular conjugate thereof, and methods of using a biomolecular conjugate for ultrasensitive nonisotopic detection in vitro and in vivo.

16 Claims, 4 Drawing Sheets

OTHER PUBLICATIONS

Mahtab et al., "Preferential–Absorption of a 'Kinked' DNA to a Neutral Curved Surface: Comparison to and Implications for Nonspecific DNA–Protein Interactions," *J. Am. Chem. Soc.,* 118, 7028–7032 (1996).

Mikulec et al., *Mat. Res. Soc. Symp.,* 452, 359–364 (1997).

Murphy et al., "Quantum Dots as Inorganic DNA–Binding Proteins," *Mat. Res. Soc. Symp.,* 452, 597–600 (1997).

Nicolaou et al., "Radiofrequency Encoded Cominatorial Chemistry," *Ignew. Chem. Int. Ed. Engl.,* 34, 2289–2291 (1991).

Peng et al., "Epitaxial Growth of Highly Luminescent CdSe/Cds Core/Shell Nanocrystals with Photostability and Electronic Accessibilty," *J. Am. Chem. Soc.,* 119, 7019–1029 (1997).

Shrock et al., "Multicolor Spectral Karyotyping of Human Chromosomes," *Science,* 273, 494–497 (1996).

Whitesell et al., "Directionally Aligneed Helical Peptides on Surfaces," *Science,* 261, 73–76 (1993).

Zhang et al., "Novel Flow Cytometry Compensation Standards: Internally Stained Fluorescent Microspheres with Matched Emission Spectra and Long–Term Stability," *Cytometry,* 33, 244–248 (1998).

Alivisatos, "Semiconductor Clusters, Nanocrystals, and Quantum Dots," *Science,* 271, 933–37 (1996).

Alivisatos, "Perspectives on the Physical Chemistry of Semiconductor Nanocrystals," *J. Phys. Chem.,* 100, 13226–39 (1996).

Blanton et al., "Photoluminescence Wandering in Single CdSe Nanocrystals," *Appl. Phys. Lett.,* 69, 3905 (1996).

Bowden Katari et al., "X–ray Photoelectron Spectroscopy of CdSe Nanocrystals with Applications to Studies of the Nanocrystal Surfaces," *J. Phys. Chem.,* 98, 4109–4117 (1994).

Brus, "Quantum Crystallites and Nonlinear Optics," *Appl. Phys.,* A 53, 465–74 (1991).

Dabbousi et al., "(CdSe)ZnS Core–Shell Quantum Dots: Synthesis and Characterization of a Size Serries of Highly Luminescent Nanocrystallites," *J. Phys. Chem.,* B 101, 9463–75 (1997).

Edwards et al., "Thew Nucleation of Receptor–Mediated Endocytosis," *PNAS,* 93(5), 1786–1791 (1996).

Empedocles et al., "Photoluminescence Spectroscopy of Single CdSe Nanocrystalliter Quantum Dots," *Phys. Rev. Lett.,* 77, 3873 (1996).

Henglein, "Small–Particle Research: Physicochemical Properties of Extremely Small Colloidal Metal and Semiconductor Particles," *Chem. Rev.,* 89, 1861–73 (1989).

Hines et al., "Synthesis and Characterization of Strongly Luminescing ZnS–Capped CdSe Nanocrystals," *J. Phys. Chem.,* 100, 468–71 (1996).

Lee et al., "Surface Derivatization of Nanocrystalline CdSe Semiconductors," *Mat. Res. Soc. Symp. Proc.,* 452, 232–328 (1997).

Mikulec et al., "Fluorescent Semiconductor Nanocrystallites Derivatized with Biomolecules," *Abst. Papers of Am. Chem. Soc.,* 216(3), P 018 MACR (1998).

Murray et al., "Synthesis and Characterization of Nearly Monodisperse CdE (E=S, Se, Te) Semiconductor Nanocrystallites," *J. Am. Chem. Soc.,* 115, 8706–8715 (1993).

Nirmal et al., "Fluorescence Intermittency in Single Cadmium Selenide Nanocrystals," *Nature,* 383, 802 (1996).

Smythe et al., "The Mechanism of Receptor–Mediated Endocytosis," *Eur. J. Biochem.,* 202, 689(1991).

Weller, "Colloidal Semiductor Q–Particle: Chemistry in the Transition Region Between Solid State and Molecules," *Angew. Chem. Int. Ed. Engl.,* 32, 41–53 (1993).

Wilson et al., "Quantum Confinement in Sized–Selected, Surface–Oxidized Silicon Nanocrystals," *Science,* 262, 1242–46 (1993).

* cited by examiner

WATER-SOLUBLE LUMINESCENT QUANTUM DOTS AND BIOMOLECULAR CONJUGATES THEREOF AND RELATED COMPOSITIONS AND METHOD OF USE

This application claims priority to U.S. provisional patent application Ser. No. 60/101,748, filed Sep. 24, 1998, and U.S. provisional patent application Ser. No. 60/131,987, filed Apr. 30, 1999.

GOVERNMENT SUPPORT

This invention was made, in part, with funding from the National Science Foundation under Grant No. CHE-9610254 and from the Department of Energy under Grant No. FG02-98ER14873. Therefore, the United States of America may have certain rights in the invention.

TECHNICAL FIELD OF INVENTION

The present invention relates to a water-soluble luminescent quantum dot, a biomolecular conjugate thereof and a composition comprising such a quantum dot or conjugate. Additionally, the present invention relates to a method of obtaining a luminescent quantum dot, a method of making a biomolecular conjugate thereof, and methods of using a biomolecular conjugate for ultrasensitive nonisotopic detection in vitro and in vivo.

BACKGROUND OF THE INVENTION

The development of sensitive nonisotopic detection systems for use in biological assays has significantly impacted many research and diagnostic areas, such as DNA sequencing, clinical diagnostic assays, and fundamental cellular and molecular biology protocols. Current nonisotopic detection methods are mainly based on organic reporter molecules that undergo enzyme-linked color changes or are fluorescent, luminescent, or electroactive (Kricka, Ed., *Nonisotopic Probing, Blotting, and Sequencing*, Academic Press, New York, 1995; Issac, Ed., *Protocols for Nucleic Acid Analysis by Nonradioactive Probes*, Humana, Totowa, N.J., 1994; and Diamandis and Christopoulos, Eds., *Immunoassay*, Academic Press, New York, 1996). While these nonisotopic systems solve the problems associated with radioisotopic detection, such as short half-lives of radioisotopes, health hazards and expensive removal of radioactive waste, they are not as sensitive or stable as nonisotopic detection systems that utilize luminescent semiconductor quantum dots. For example, highly luminescent semiconductor quantum dots, such as ZnS-capped CdSe quantum dots, are twenty times brighter, one hundred times more stable against photobleaching, and three times narrower in spectral line width than organic dyes, such as fluorescent rhodamine.

Over the past decade, much progress has been made in the synthesis and characterization of a wide variety of semiconductor quantum dots. Recent advances have led to large-scale preparation of relatively monodisperse quantum dots (Murray et al., *J. Am. Chem. Soc.*,115, 8706–15 (1993); Bowen Katari et al., *J. Phys. Chem.*, 98, 4109–17 (1994); and Hines et al.,*J. Phys. Chem.*, 100, 468–71 (1996)). Other advances have led to the characterization of quantum dot lattice structures (Henglein, *Chem. Rev.*, 89, 1861–73 (1989); and Weller et al., *Chem. Int. Ed. Engl.* 32, 41–53 (1993)) and also to the fabrication of quantum-dot arrays (Murray et al., *Science*, 270, 1335–38 (1995); Andres et al., *Science*, 273, 1690–93 (1996); Heath et al., *J. Phys. Chem.*, 100, 3144–49 (1996); Collier et al., *Science*, 277, 1978–81 (1997); Mirkin et al., *Nature*, 382, 607–09 (1996); and Alivisatos et al., *Nature*, 382, 609–11 (1996)) and light-emitting diodes (Colvin et al., *Nature*, 370, 354–57 (1994); and Dabbousi et al., *Appl. Phys. Let.*, 66, 1316–18 (1995)). In particular, IIB–VIB semiconductors have been the focus of much attention, leading to the development of a CdSe quantum dot that has an unprecedented degree of monodispersivity and crystalline order (Murray (1993), supra).

Further advances in luminescent quantum dot technology have resulted in a dramatic enhancement of the fluorescence efficiency and stability of the quantum dots. The remarkable luminescent properties of quantum dots arise from quantumsize confinement, which occurs when metal and semiconductor core particles are smaller than their exciton Bohr radii, about 1 to 5 nm (Alivisatos, *Science*, 271, 933–37 (1996); Alivisatos, *J. Phys. Chem.*, 100, 13226–39 (1996); Brus, *Appl. Phys.*, A 53, 465–74 (1991); Wilson et al., *Science*, 262, 1242–46 (1993); Henglein (1989), supra; and Weller (1993), supra). Recent work has shown that improved luminescence can be achieved by capping a size-tunable lower band gap core particle with a higher band gap shell. For example, CdSe quantum dots passivated with a ZnS layer are strongly luminescent (35 to 50% quantum yield) at room temperature, and their emission wavelength can be tuned from blue to red by changing the particle size. Moreover, the ZnS capping protects the core surface and leads to greater stability of the quantum dot (Hines (1996), supra; and Dabbousi et al., *J. Phys. Chem.* B 101, 9463–75 (1997)).

Despite the remarkable advances in luminescent quantum dot technology, the capped luminescent quantum dots are not suitable for biological applications because they are not water-soluble. In addition, it has not been possible to attach a quantum dot to a biomolecule in such a manner as to preserve the biological activity of the biomolecule. However, because luminescent quantum dots offer significant advantages over currently available nonisotopic detection systems, there remains an unfulfilled desire for a luminescent quantum dot that can be used for detection purposes in biological assays. In view of this, it is an object of the present invention to provide a luminescent quantum dot that is suitable for biological applications. It is another object of the present invention to provide a biomolecular conjugate of a luminescent quantum dot that is suitable for biological applications. In particular, the present invention seeks to provide a biomolecular conjugate of a luminescent quantum dot in which the biomolecule retains its biological activity and the resultant conjugate is suitable for biological applications. Accordingly, it is yet another object of the present invention to provide a method of making such a luminescent quantum dot and a method of making a biomolecular conjugate thereof. Still yet another object of the present invention is to provide a composition comprising such a quantum dot or a biomolecular conjugate thereof. A further object of the present invention is to provide methods of using the biomolecular conjugate for ultrasensitive nonisotopic detection in vitro and in vivo. These and other objects and advantages, as well as additional. inventive features, of the present invention will become apparent to one of ordinary skill in the art upon reading the detailed description provided herein.

BRIEF SUMMARY OF THE PRESENT INVENTION

The present invention provides a water-soluble luminescent quantum dot, which comprises a core, a cap and a hydrophilic attachment group. Also provided is a composition comprising the water-soluble luminescent quantum dot and an aqueous carrier. The present invention further provides a conjugate, which comprises the water-soluble luminescent quantum dot and a biomolecule, wherein the biomolecule is attached directly or indirectly to the hydrophilic attachment group. Also provided is a composition comprising the conjugate and an aqueous carrier.

Further provided by the present invention are a method of obtaining a watersoluble luminescent quantum dot and methods of making biomolecular conjugates thereof. Other methods provided by the present invention include methods of detecting biomolecules in vitro and in vivo.

DETAILED DESCRIPTION OF THE PRESENT INVENTION

Figure 1:
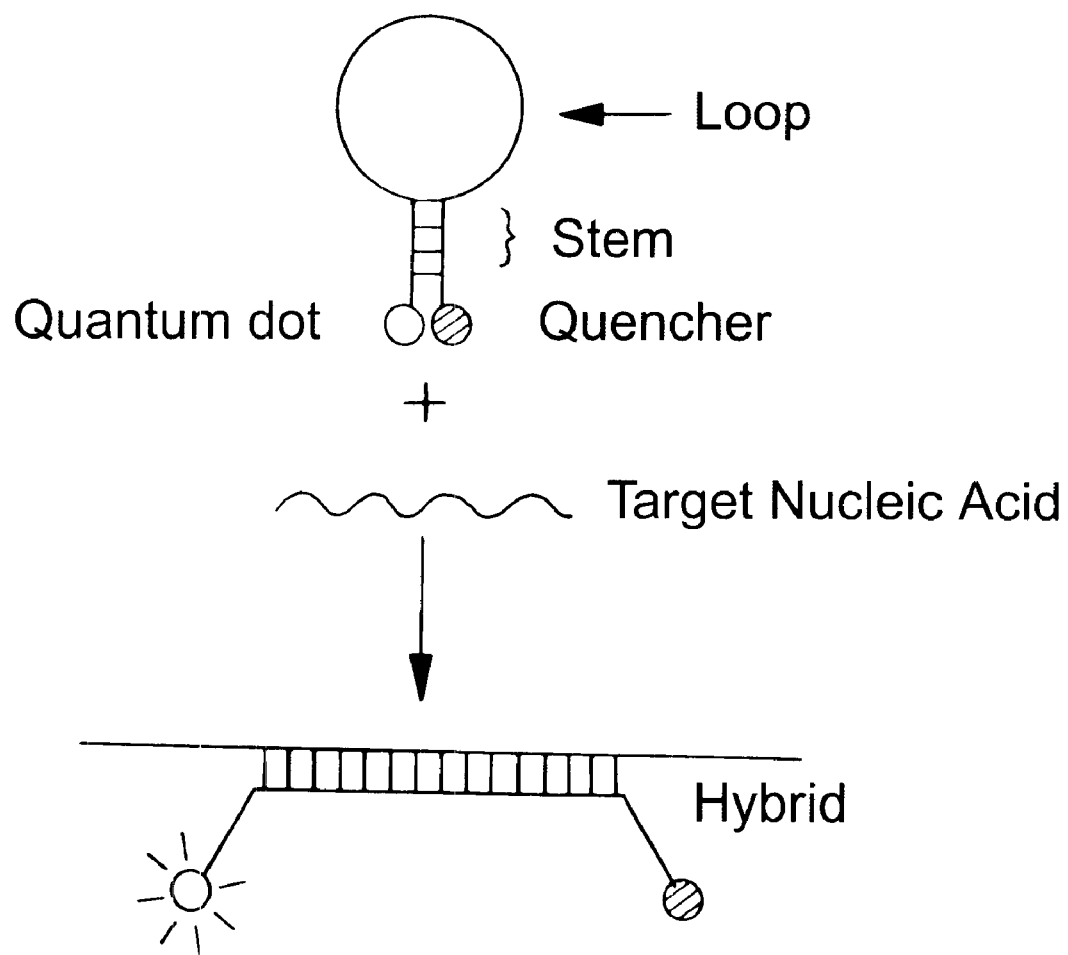
FIG. 1 is a schematic diagram of a bioconjugate comprising a single-stranded oligonucleotide having a stem and loop structure and the bioconjugate bound to a target nucleic acid.

The present invention provides means and methods of ultrasensitive nonisotopic detection of biomolecules in vitro and in vivo. The present invention is premised on the surprising, unexpected and advantageous discovery that capped luminescent quantum dots can be rendered water-soluble by attaching a hydrophilic attachment group to the cap of the quantum dot and that these quantum dots retain their luminescent properties. The present invention is also premised on the discovery that various biomolecules can be directly and indirectly attached to the hydrophilic attachment group on the cap of the quantum dot and that these biomolecules can retain their biological activity.

In view of the above, the present invention provides, in one embodiment, a water-soluble luminescent semiconductor quantum dot, which comprises a core, a cap and a hydrophilic attachment group. The "core" is a nanoparticle-sized semiconductor. While any core of the IIB–VIB, IIIB–VB or IVB—IVB semiconductors can be used in the context of the present invention, the core must be such that, upon combination with a cap, a luminescent quantum dot results. A IIB–VIB semiconductor is a compound that contains at least one element from Group IIB and at least one element from Group VIB of the periodic table, and so on. Preferably, the core is a IIB–VIB, IIIB–VB or IVB—IVB semiconductor that ranges in size from about 1 nm to about 10 nm. The core is more preferably a IIB–VIB semiconductor and ranges in size from about 2 nm to about 5 nm. Most preferably, the core is CdS or CdSe. In this regard, CdSe is especially preferred as the core, in particular at a size of about 4.2 nm.

The "cap" is a semiconductor that differs from the semiconductor of the core and binds to the core, thereby forming a surface layer on the core. The cap must be such that, upon combination with a given semiconductor core, results in a luminescent quantum dot. The cap should passivate the core by having a higher band gap than the core. In this regard, the cap is preferably a IIB–VIB semiconductor of high band gap. More preferably, the cap is ZnS or CdS. Most preferably, the cap is ZnS. In particular, the cap is preferably ZnS when the core is CdSe or CdS and the cap is preferably CdS when the core is CdSe.

The "attachment group" as that term is used herein refers to any organic group that can be attached, such as by any stable physical or chemical association, to the surface of the cap of the luminescent semiconductor quantum dot and can render the quantum dot water-soluble without rendering the quantum dot no longer luminescent. Accordingly, the attachment group comprises a hydrophilic moiety. Preferably, the attachment group enables the hydrophilic quantum dot to remain in solution for at least about one hour. More preferably the attachment group enables the hydrophilic quantum dot to remain in solution for at least about one day. Even more preferably, the attachment group allows the hydrophilic quantum dot to remain in solution for at least about one week, most preferably for at least about one month. Desirably, the attachment group is attached to the cap by covalent bonding and is attached to the cap in such a manner that the hydrophilic moiety is exposed. Preferably, the hydrophilic attachment group is attached to the quantum dot via a sulfur atom. More preferably, the hydrophilic attachment group is an organic group comprising a sulfur atom and at least one hydrophilic attachment group. Suitable hydrophilic attachment groups include, for example, a carboxylic acid or salt thereof, a sulfonic acid or salt thereof, a sulfamic acid or salt thereof, an amino substituent, a quaternary ammonium salt, and a hydroxy. The organic group of the hydrophilic attachment group of the present invention is preferably a $C_1$–$C_6$ alkyl group or an aryl group, more preferably a $C_1$–$C_6$ alkyl group, even more preferably a $C_1$–$C_3$ alkyl group. Therefore, in a preferred embodiment, the attachment group of the present invention is a thiol carboxylic acid or thiol alcohol. More preferably, the attachment group is a thiol carboxylic acid. Most preferably, the attachment group is mercaptoacetic acid.

Accordingly, a preferred embodiment of a water-soluble luminescent semiconductor quantum dot is one that comprises a CdSe core of about 4.2 nm in size, a ZnS cap and an attachment group. Another preferred embodiment of a water-soluble luminescent semiconductor quantum dot is one that comprises a CdSe core, a ZnS cap and the attachment group mercaptoacetic acid. An especially preferred water-soluble luminescent semiconductor quantum dot comprises a CdSe core of about 4.2 nm, a ZnS cap of about 1 nm and a mercaptoacetic acid attachment group.

In another embodiment, the present invention also provides a composition comprising a water-soluble luminescent semiconductor quantum dot as described above and an aqueous carrier. Any suitable aqueous carrier can be used in the composition. Desirably, the carrier renders the composition stable at a desired temperature, such as room temperature, and is of an approximately neutral pH. Examples of suitable aqueous carriers are known to those of ordinary skill in the art and include saline solution and phosphate-buffered saline solution (PBS).

In yet another embodiment, the present invention provides a conjugate comprising a water-soluble luminescent semiconductor quantum dot as described above and a biomolecule, wherein the biomolecule is attached to the quantum dot via the hydrophilic attachment group. The biomolecule should not render the quantum dot water-insoluble. Preferably, the biomolecule is a protein, a fragment of a protein, or a nucleic acid. Use of the phrase "protein or a fragment thereof" is intended to encompass a protein, a glycoprotein, a polypeptide, a peptide, and the like, whether isolated from nature, of viral, bacterial, plant or animal (e.g., mammalian, such as human) origin, or synthetic. A preferred protein or fragment thereof for use as a biomolecule in the present inventive conjugate is an antigen, an epitope of an antigen, an antibody, or an antigenically reactive fragment of an antibody. Use of the phrase "nucleic acid" is intended to encompass DNA and RNA, whether isolated from nature, of viral, bacterial, plant or animal (e.g., mammalian, such as human) origin, synthetic, single-stranded, double-stranded, comprising naturally or nonnaturally occurring nucleotides, or chemically modified. A preferred nucleic acid is a singlestranded oligonucleotide comprising a stem and loop structure and the hydrophilic attachment group is attached to one end of the single-stranded oligonucleotide and a quenching moiety is attached to the other end of the single-stranded oligonucleotide and the quenching moiety quenches the luminescent semiconductor quantum dot.

The biomolecule can be attached, such as by any stable physical or chemical association, to the hydrophilic attachment group of the water-soluble luminescent quantum dot directly or indirectly by any suitable means. Desirably, the biomolecule is attached to the attachment group directly or indirectly through one or more covalent bonds. If the biomolecule is attached to the hydrophilic attachment group indirectly, the attachment preferably is by means of a "linker." Use of the term "linker" is intended to encompass any suitable means that can be used to link the biomolecule to the attachment group of the water-soluble luminescent quantum dot. The linker should not render the water-soluble luminescent quantum dot water-insoluble and should not adversely affect the luminescence of the quantum dot. Also, the linker should not adversely affect the function of the attached biomolecule. If the conjugate is to be used in vivo, desirably the linker is biologically compatible.

For example, if the attachment group is mercaptoacetic acid and a nucleic acid biomolecule is being attached to the attachment group, the linker preferably is a primary amine, a thiol, streptavidin, neutravidin, biotin, or a like molecule. If the attachment group is mercaptoacetic acid and a protein biomolecule or a fragment thereof is being attached to the attachment group, the linker preferably is strepavidin, neutravidin, biotin, or a like molecule. In accordance with the invention, the linker should not contact the protein biomolecule or a fragment thereof at an amino acid which is essential to the function or activity of the attached protein. Crosslinkers, such as intermediate crosslinkers, can be used to attach a biomolecule to the attachment group of the water-soluble luminescent quantum dot. Ethyl-3-(dimethylaminopropyl) carbodiimide (EDAC) is an example of an intermediate crosslinker. Other examples of intermediate crosslinkers for use in the present invention are known in the art. See, for example, *Bioconjugate Techniques* (Academic Press, New York, (1996)).

Catalytic crosslinkers also can be used to attach a biomolecule to the attachment group of the water-soluble luminescent quantum dot. Catalytic crosslinkers effect direct attachment of the biomolecule to the attachment group. Examples of catalytic crosslinkers are also known in the art. See, for example, *Bioconjugate Techniques* (1996), supra.

Attachment of a biomolecule to the attachment group of the water-soluble luminescent quantum dot also can be effected by a bi-functional compound as is known in the art. See, for example, *Bioconjugate Techniques* (1996), supra.

In those instances where a short linker could cause steric hindrance problems or otherwise affect the functioning of the biomolecule, the length of the linker can be increased, e.g., by the addition of from about a 10 to about a 20 atom spacer, using procedures well-known in the art (see, for example, *Bioconjugate Techniques* (1996), supra). One possible linker is activated polyethylene glycol, which is hydrophilic and is widely used in preparing labeled oligonucleotides.

Accordingly, a preferred conjugate in accordance with the present invention is a conjugate comprising a CdSe core of about 4.2 nm, a ZnS cap, a hydrophilic attachment group and a biomolecule. Another preferred conjugate in accordance with the present invention is a conjugate comprising a CdSe core, a ZnS cap, a mercaptoacetic acid attachment group and a biomolecule. An especially preferred conjugate comprises a CdSe core of about 4.2 nm, a ZnS coating of about 1 nm, a mercaptoacetic acid attachment group and a biomolecule.

An alternatively preferred conjugate in accordance with the present invention is a conjugate essentially as described above, wherein the biomolecule is a single-stranded oligonucleotide comprising a stem and a loop. The hydrophilic attachment group is attached to one end of the single-stranded oligonucleotide, and a quenching moiety is attached to the other end of the single-stranded oligonucleotide. The quenching moiety quenches the luminescent semiconductor quantum dot.

Any suitable quenching moiety that quenches the luminescence of the quantum dot can be used in the alternatively preferred conjugate described above. Preferably, the alternatively preferred conjugate comprises a primary amine group at the 3' end and a biotin group at the 5' end. The quenching moiety is preferably a nonfluorescent organic chromophore, which is covalently linked to the 3' amino group of the oligonucleotide. More preferably, the quenching moiety is 4-[4'-dimethylaminophenylazo]benzoic acid (DABCYL). Preferably, the luminescent quantum dot of the bioconjugate is first derivatized with streptavidin according to well-known cross-linking methods and then conjugated to the 5' biotin group, preferably at a 1:1 molar ratio.

Thus, in another embodiment, the present invention also provides a composition comprising a conjugate as described above and an aqueous carrier. Any suitable aqueous carrier can be used in the composition. Desirably, the carrier renders the composition stable at a desired temperature, such as room temperature, and is of an approximately neutral pH. Examples of suitable aqueous carriers are known to those of ordinary skill in the art and include saline solution and PBS.

In view of the above, the present invention further provides a method of obtaining a water-soluble luminescent semiconductor quantum dot as described. The method comprises (a) reacting a luminescent semiconductor quantum dot as described above in a nonpolar organic solvent with a first aqueous solution comprising an attachment group; (b) adding a second aqueous solution of about neutral pH and mixing; and (c) extracting an aqueous layer, thereby obtaining a water-soluble luminescent semiconductor quantum dot. Preferably, the nonpolar organic solvent is chloroform and the attachment group is mercaptoacetic acid.

The present invention also provides a method of making a conjugate comprising a water-soluble luminescent semiconductor quantum dot and a biomolecule as described above. Where the biomolecule is to be directly attached to the attachment group of the quantum dot, the method comprises (a) contacting a water-soluble luminescent semiconductor quantum dot as described above with a biomolecule, which can directly attach to the attachment group on the cap of the water-soluble luminescent semiconductor quantum dot; and (b) isolating the conjugate. Preferably, the biomolecule is a protein or a fragment thereof or a nucleic acid. In one embodiment of the method of directly attaching the biomolecule to the attachment group, the attachment group is mercaptoacetic acid and the biomolecule is a protein. In another embodiment of the direct attachment method, the quantum dot and the biomolecule are contacted in the presence of a catalytic crosslinker.

Where the biomolecule is to be indirectly attached to the attachment group of the water-soluble luminescent semiconductor quantum dot, the present invention provides a method comprising (a) contacting a water-soluble semiconductor luminescent quantum dot as described above with a linker, which can attach to the attachment group and the biomolecule; (b) isolating the water-soluble luminescent semiconductor quantum dot to which is attached a linker; (c) contacting the water-soluble luminescent semiconductor quantum dot to which is attached a linker with a biomolecule; and (d) isolating the conjugate.

Alternatively, the method comprises (a) contacting a biomolecule with a linker, which can attach to the attachment group and the biomolecule; (b) isolating the biomolecule to which is attached a linker; (c) contacting the biomolecule to which is attached a linker with a water-soluble luminescent quantum dot; and (d) isolating the conjugate. In one embodiment of the method of indirectly attaching the biomolecule to the attachment group, the linker is a primary amine or streptavidin, the attachment group is mercaptoacetic acid and the biomolecule is a nucleic acid.

In another embodiment of the method of indirectly attaching the biomolecule to the attachment group, the method comprises (a) contacting a water-soluble luminescent quantum dot with an intermediate crosslinker or a bifunctional molecule, either one of which can attach to the attachment group and the biomolecule; (b) isolating the water-soluble luminescent quantum dot to which is attached the intermediate crosslinker or the bifunctional molecule; (c) contacting the water-soluble luminescent quantum dot to which is attached the intermediate crosslinker or the bifunctional molecule with a biomolecule; and (d) isolating the conjugate.

Alternatively, the method comprises (a) contacting a biomolecule with an intermediate crosslinker or a bifunctional molecule, either one of which can attach to the attachment group and the biomolecule; (b) isolating the biomolecule to which is attached the intermediate crosslinker or the bifunctional molecule; (c) contacting the biomolecule to which is attached the intermediate crosslinker or the bifunctional molecule with a water-soluble luminescent quantum dot; and (d) isolating the conjugate. An example of such an embodiment is a method employing mercaptoacetic acid as the attachment group, a protein or a fragment thereof as the biomolecule, and EDAC as the intermediate crosslinker.

Also provided by the present invention is a method of detecting a protein in a sample. The method comprises (a) contacting the sample with a conjugate as described above, wherein the biomolecule of the conjugate specifically binds to the protein; and (b) detecting luminescence, wherein the detection of luminescence indicates that the conjugate bound to the protein in the sample.

Preferably, in the method of protein detection, the biomolecule of the conjugate is a protein or a fragment thereof, such as an antibody or an antigenically reactive fragment thereof, and the protein in the sample is an antigen or an epitope thereof that is bound by the antibody or an antigenically reactive fragment thereof. The antigen or epitope thereof preferably is part of a virus or a bacterium. Alternatively and preferably, the biomolecule of the conjugate is an antigen or an epitope thereof and the protein in the sample is an antibody or an antigenically reactive fragment thereof that binds to the antigen or epitope thereof. The antibody or the antigenically reactive fragment thereof preferably is specific for a virus, a bacterium, or a part of a virus or a bacterium. In yet another alternative and preferred embodiment, the biomolecule of the conjugate is a nucleic acid and the protein in the sample is a nucleic acid binding protein, e.g., a DNA binding protein.

Another method provided by the present invention is a method of detecting a nucleic acid in a sample. The method comprises (a) contacting the sample with a conjugate as described above, wherein the biomolecule of the conjugate specifically binds to the nucleic acid; and (b) detecting luminescence, wherein the detection of luminescence indicates that the conjugate bound to the nucleic acid in the sample. Preferably, the biomolecule of the conjugate is a nucleic acid. Alternatively and preferably, the biomolecule of the conjugate is a protein or a fragment thereof that binds to a nucleic acid, such as a DNA binding protein.

As shown in FIG. 1, the present invention also provides another method of detecting a nucleic acid in a sample. This method involves the use of a bioconjugate comprising a single-stranded oligonucleotide having a stem-and-loop structure, a quantum dot moiety, and a quenching moiety. The loop of the oligonucleotide comprises a probe sequence that is complementary to a target sequence in the nucleic acid to be detected in a sample. Desirably, the loop is of sufficient size such that it opens readily upon contact with a target sequence, yet not so large that it is easily sheared. Preferably, the loop is from about 10 nucleotides to about 30 nucleotides and more preferably from about 15 nucleotides to about 25 nucleotides. The probe sequence can comprise all or less than all of the loop. Preferably, the probe sequence is at least about 15 nucleotides in length. The stem is formed by the annealing of complementary sequences that are at or near the two ends of the single-stranded oligonucleotide. A luminescent quantum dot moiety is covalently linked to one end of the single-stranded oligonucleotide and a quenching moiety is covalently linked to the other end of the single-stranded oligonucleotide. The stem keeps the luminescent quantum dot and quenching moieties in close proximity to each other so that the luminescence of the quantum dot is quenched when the single-stranded oligonucleotide is not bound to a target sequence. In this regard, the complementary sequences of which the stem is comprised must be sufficiently close to the ends of the oligonucleotide as to effect quenching of the luminescent quantum dot. When the probe sequence encounters a target sequence in a nucleic acid to be detected in a sample, it binds, i.e., hybridizes, to the target sequence, thereby forming a probe-target hybrid that is longer and more stable than the stem hybrid. The length and rigidity of the probe-target hybrid prevents the simultaneous formation of the stem hybrid. As a result, the structure undergoes a spontaneous conformational change that forces the stem to open, thereby separating the quantum dot moiety and the quenching moiety and restoring luminescence.

Accordingly, the method comprises (a) contacting the sample with a conjugate, in which the biomolecule is a single-stranded oligonucleotide comprising a stem-and-loop structure and in which the hydrophilic attachment group is attached to one end of the single-stranded oligonucleotide and a quenching moiety is attached to the other end of the single-stranded oligonucleotide, such that the quenching moiety quenches the luminescent semiconductor quantum dot, all as described above. The loop comprises a probe sequence that binds to a target sequence in the nucleic acid in the sample. Upon binding, the conjugate undergoes a conformational change that forces the stem to open, thereby separating the quantum dot and the quenching moiety. The method further comprises (b) detecting luminescence. The detection of luminescence indicates that the conjugate bound to the nucleic acid in the sample.

Figure 2:
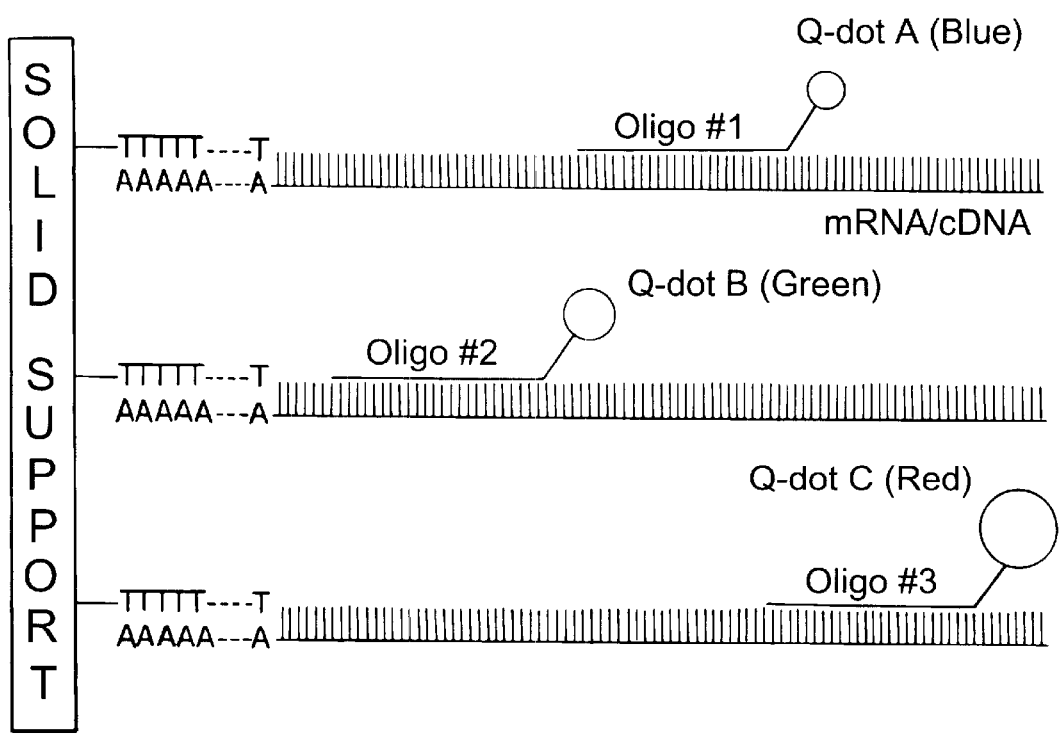
FIG. 2 is a schematic diagram of a method of detecting multiple nucleic acids in a sample in accordance with the present invention.

As shown in FIG. 2, the present invention provides yet another method of detecting a single-stranded nucleic acid, such as mRNA, cDNA, or denatured double-stranded DNA in a sample, by attachment to a solid support, such as a membrane, glass bead, transparent polymer and the like. The method comprises (a) contacting a sample comprising a first single-stranded nucleic acid with a solid support to which is attached a second single-stranded nucleic acid that can bind to the first single-stranded nucleic acid, (b) contacting the solid support with a conjugate as described above, in which the biomolecule is a third single-stranded nucleic acid that specifically binds to the first single-stranded nucleic acid in a region other than that which is bound by the second single-stranded nucleic acid; and (c) detecting luminescence, wherein the detection of luminescence indicates that the third single-stranded nucleic acid of the conjugate bound to the first single-stranded nucleic acid in the sample.

Preferably, the second single-stranded nucleic acid is an oligonucleotide capture probe, such as a synthetic thymine (poly-T) or adenosine (poly-A) oligonucleotide. Preferably, the second single-stranded nucleic acid is attached to the solid support by standard crosslinking procedures in accordance with methods known in the art (see, e.g., Joos et al., *Anal. Biochem.*, 247, 96–101 (1997); Running et al., *BioTechniques*, 8, 276–277 (1990)). The second single-stranded nucleic acid should be of sufficient length and density on the solid support so as to bind stably and efficiently with the first single-stranded nucleic acid. Preferably, the capture probe is at least about 35 bases in length.

More broadly, the present invention provides a method of detecting a nucleic acid in a sample. The method comprises attaching a nucleic acid capture probe to a solid support. The nucleic acid capture probe comprises a sequence that binds to the nucleic acid in the sample. The attached nucleic acid capture probe is then contacted with the sample, thereby immobilizing the nucleic acid on the solid support. The method further comprises contacting the immobilized nucleic acid with a conjugate comprising a water-soluble luminescent semiconductor quantum dot and a biomolecule. The biomolecule of the conjugate specifically binds to the nucleic acid. Then, the method comprises detecting luminescence. The detection of luminescence indicates that the conjugate bound to the nucleic acid in the sample.

The present invention also provides a method whereby two or more different molecules and/or two or more regions on a given molecule can be simultaneously detected in a sample. The method involves using a set of conjugates as described above, wherein each of the conjugates in the set has a differently sized quantum dot or a quantum dot of different composition attached to a biomolecule that specifically binds to a different molecule or a different region on a given molecule in the sample. Preferably, the quantum dots of the conjugates range in size from 1 nm to 10 nm, which sizes allow the emission of luminescence in the range of blue to red. The quantum dot size that corresponds to a particular color emission is well-known in the art. Within this size range, any size variation of quantum dot can be used as long as the differently sized quantum dots can be excited at a single wavelength and differences in the luminescence between the differently sized quantum dots can be detected. Desirably, the differently sized quantum dots have a capping layer that has a narrow and symmetric emission peak. Preferably, the differently sized quantum dots have an inorganic capping layer that matches the structure of the core. More preferably, the differently sized quantum dots have a ZnS or a CdSe capping layer. Similarly, quantum dots of different composition or configuration will vary with respect to particular color emission. Any variation of composition between quantum dots can be used as long as the quantum dots differing in composition can be excited at a single wavelength and differences in the luminescence between the quantum dots of different composition can be detected. Detection of the different target molecules in the sample arises from the emission of multicolored luminescence generated by the quantum dots differing in composition or the differently sized quantum dots of which the set of conjugates is comprised. This method also enables different functional domains of a single protein, for example, to be distinguished.

Accordingly, the present invention provides a method of simultaneously detecting two or more different molecules and/or two or more regions of a given molecule in a sample. The method comprises contacting the sample with two or more conjugates of a water-soluble luminescent semiconductor quantum dot and a biomolecule, wherein each of the two or more conjugates comprises a quantum dot of a different size or composition and a biomolecule that specifically binds to a different molecule or a different region of a given molecule in the sample. The method further comprises detecting luminescence, wherein the detection of luminescence of a given color is indicative of a conjugate binding to a molecule in the sample.

In accordance with the present invention, two or more proteins or fragments thereof can be simultaneously detected in a sample. Alternatively, two or more nucleic acids can be simultaneously detected. In this regard, a sample can comprise a mixture of nucleic acids and proteins (or fragments thereof).

Preferably, in the method of detecting two or more proteins or fragments thereof, the biomolecule of each of the conjugates is a protein or a fragment thereof, such as an antibody or an antigenically reactive fragment thereof, and the proteins or fragments thereof in the sample are antigens or epitopes thereof that are bound by the antibody or the antigenically reactive fragment thereof. Alternatively and also preferably, the biomolecules of each of the conjugates is an antigen or epitope thereof and the proteins or fragments thereof in the sample are antibodies or antigenically reactive fragments thereof that bind to the antigen or epitope thereof. Also preferably, the biomolecule of each of the conjugates is a nucleic acid and the proteins or fragments thereof in the sample are nucleic acid binding proteins, e.g., DNA binding proteins.

Also, in accordance with the present invention, two or more nucleic acids can be simultaneously detected in a sample. Any of the above-described methods for detecting a nucleic acid in a sample can be used with two or more conjugates comprising differently sized quantum dots attached to biomolecules that can bind to nucleic acids. Accordingly, one method of simultaneously detecting two or more nucleic acids in a sample comprises (a) contacting the sample with two or more conjugates, in which each conjugate comprises a differently sized quantum dot attached to a biomolecule, preferably a nucleic acid, in particular a single-stranded nucleic acid, or a protein or fragment thereof, such as a DNA binding protein, that specifically binds to a target nucleic acid in the sample; and (b) detecting luminescence, wherein the detection of luminescence of a given color indicates that a conjugate bound to its target nucleic acid in the sample.

Another method of simultaneously detecting two or more nucleic acids in a sample involves using two or more conjugates, each of which comprises a different above-described single-stranded oligonucleotide having a stem-and-loop structure, in accordance with the methods for using such a conjugate as set forth above. Yet another method of simultaneously detecting two or more nucleic acids in a sample involves using the above-described method, wherein the nucleic acids to be detected are attached to a solid support of the kind described above, in accordance with the described methods for attaching a nucleic acid in a sample and the described methods for detecting said nucleic acid as set forth above. One embodiment of this method is depicted in FIG. 2.

In another embodiment of the inventive method of simultaneously detecting two or more molecules in a sample, the sample comprises at least one nucleic acid and at least one protein or fragment thereof The simultaneous detection of a nucleic acid and a protein or fragment thereof in a sample can be accomplished using the methods described above in accordance with the described methods for detecting a protein or fragment thereof in a sample and the described methods for detecting a nucleic acid in a sample as set forth above.

The above described conjugates and methods can be adapted for use in numerous other methods and biological systems to effect the detection of a biomolecule. Such methods include, for example, in situ hybridization and the like. The present invention also has broad application for the real-time observation of cellular mechanisms in living cells, e.g. ligand-receptor interaction and molecular trafficking, due to the increased photostability of the quantum dot.

The present invention has application in various diagnostic assays, including, but not limited to, the detection of viral infection, cancer, cardiac disease, liver disease, genetic diseases, and immunological diseases. The present invention can be used in a diagnostic assay to detect certain viruses, such as HIV and Hepatitis, by, for example, (a) removing a sample to be tested from a patient; (b) contacting the sample with a water-soluble luminescent quantum dot biomolecular conjugate, wherein the biomolecule is an antibody or antigenically reactive fragment thereof that binds to the virus; and (c) detecting the luminescence, wherein the detection of luminescence indicates that the virus is present in the sample. The patient sample can be a bodily fluid, such as saliva, tears, blood, serum or urine. For example, an antibody to HIV gp120 can be used to detect the presence of HIV in a sample; alternatively, HIV gp120 can be used to detect the presence of antibodies to HIV in a sample.

The present invention also can be used in a diagnostic assay to determine ultra-low-level viral loads of certain viruses, such as HIV and Hepatitis, by detecting the viral nucleic acid. Determining the viral load of a patient is useful in instances where the number of viral particles is below the detection limits of current techniques. For example, this technique can be particularly useful for tracking ultra-low HIV levels in AIDS patients during advanced drug treatment, such as triple drug therapy, in which the viral load of the patient has been greatly reduced. The detection of viral nucleic acid can be accomplished by, for example, (a) removing a sample to be tested from a patient; (b) treating the sample to release the viral DNA or RNA; (c) contacting the sample with a water-soluble luminescent quantum dot biomolecular conjugate, wherein the biomolecule binds to the nucleic acid of the virus; and (d) detecting the luminescence, wherein the detection of luminescence indicates that the virus is present in the sample.

Figure 3:
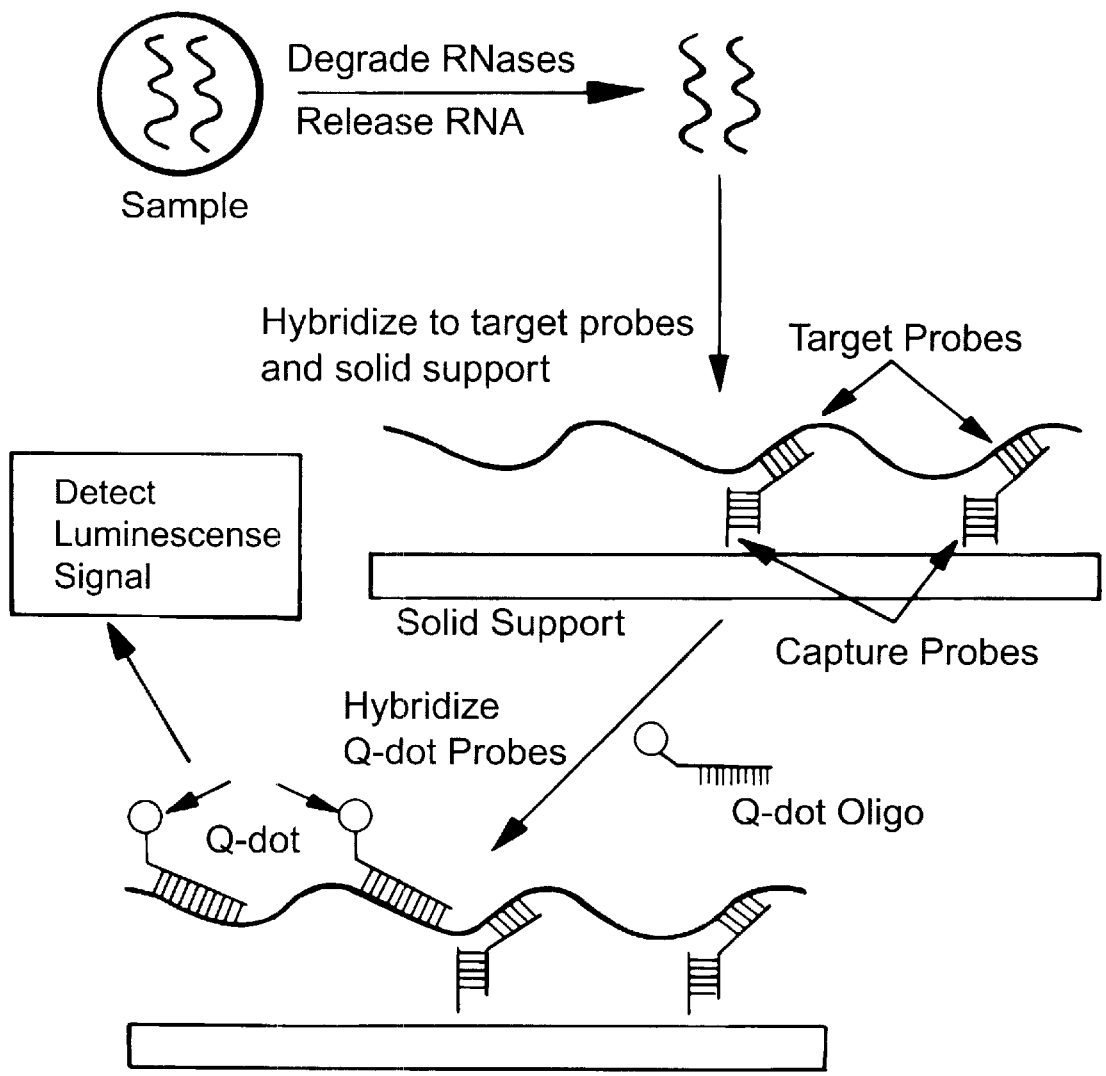
FIG. 3 is a schematic diagram of a method of detecting a viral nucleic acid in a sample in accordance with the present invention.

One embodiment of the inventive method is shown in FIG. 3. Using this method, the detection of viral nucleic acid is accomplished by (a) removing a sample to be tested from a patient; (b) treating the sample to release the viral DNA or RNA; (c) attaching capture probes to a solid support, wherein the capture probes comprise a sequence that binds to the viral nucleic acid in the sample; (d) contacting the attached capture probes with the viral nucleic acid, thereby immobilizing the viral nucleic acid on the solid support; (e) contacting the immobilized viral nucleic acid with a luminescent quantum dot conjugate, wherein the biomolecule of the conjugate specifically binds to the viral nucleic acid; and (f) detecting luminescence, wherein the detection of luminescence indicates that the conjugate bound to the viral nucleic acid in the sample.

Preferably, the solid support is a glass surface, a transparent polymer surface, a membrane, or the like, to which the capture probe can be attached. The capture probe can be any molecule that is capable of both attaching to the solid support surface and binding to the target viral nucleic acid. Preferably, the capture probe is a singlestranded oligonucleotide comprising a first nucleic acid sequence that binds to a complementary sequence attached to the solid support and a second nucleic acid sequence that binds to a third nucleic acid sequence in the viral genome. The oligonucleotide comprising the first and second nucleic acid sequences can have a length of about 20 to 50 bases. Preferably, the oligonucleotide has a length of at least about 30 bases. Desirably, the third nucleic acid sequence in the viral genome is a conserved sequence.

The luminescent quantum dot conjugate comprises a luminescent quantum dot attached to a biomolecule that specifically binds to the third sequence of the target viral nucleic acid in a region other than that which is bound by the second sequence of capture probe sequence. The biomolecule can be any molecule that can bind to the target viral nucleic acid. Preferably, the biomolecule is an oligonucleotide that contains a fourth sequence that is complementary to the third sequence in the target viral genome. Alternatively, the biomolecule can be a DNA binding protein that binds specifically to the target viral nucleic acid.

In addition to the detection of a single virus, the present invention can be used to detect simultaneously the viral load of various types of viruses or the viral load of various sub-types of a single virus by detecting the different species of viral nucleic acid. One method of simultaneously detecting multiple viral nucleic acids in a sample comprises (a) contacting the sample with a set of conjugates, wherein each conjugate of the set comprises a differently sized quantum dot attached to a probe biomolecule that specifically binds to a target viral nucleic acid in the sample; and (b) detecting the multicolored luminescence, wherein the detection of multicolored luminescence indicates that each of the differently conjugates bound to its target viral nucleic acid in the sample. Yet another method of simultaneously detecting two or more nucleic acids in a sample involves using the above-described method, which is also depicted in FIG. 3.

The present invention can be used in a similar manner to detect certain disease states, such as, for example, cancer, cardiac disease or liver disease, by (a) removing a sample to be tested from a patient; (b) contacting the sample with a water-soluble luminescent quantum dot biomolecular conjugate, wherein the biomolecule is an antibody or antigenically reactive fragment thereof that binds to a protein associated with a given disease state, wherein the disease is, for example, cancer, cardiac disease or liver disease; and (c) detecting the luminescence, wherein the detection of luminescence indicates the existence of a given disease state. In these cases, the sample can be a cell or tissue biopsy or a bodily fluid, such as blood, serum or urine. The protein can be a marker or enzyme associated with a given disease, the detection of which indicates the existence of a given disease state. The detection of a disease state can be either quantitative, as in the detection of an over- or underproduction of a protein, or qualitative, as in the detection of a non-wild-type (mutated or truncated) form of the protein. In regard to quantitative measurements, preferably the luminescence of the quantum dot conjugate-target protein complex is compared to a suitable set of standards. A suitable set of standards comprises, for example, the luminescent quantum dot conjugate of the present invention in contact with various, predetermined concentrations of the target being detected. One of ordinary skill in the art will appreciate that an estimate of, for example, amount of protein in a sample, can be determined by comparison of the luminescence of the sample and the luminescence of the appropriate standards.

The present invention also can be used to detect a disease state, such as a genetic disease or cancer, by (a) removing a sample to be tested from a patient; (b) contacting the sample with water-soluble luminescent quantum dot biomolecular conjugate, wherein the biomolecule is a nucleic acid that specifically hybridizes with a nucleic acid of interest; and (c) detecting the luminescence, wherein the detection of luminescence indicates the existence of a given disease state. In these cases, the sample can be a derived from a cell, tissue or bodily fluid. The gene of interest can be a marker for a disease-state, such as $BRCA_1$, which may indicate the presence of breast cancer.

The above-described methods also can be adapted for in vivo testing in an animal. The conjugate should be administered to the animal in a biologically acceptable carrier. The route of administration should be one that achieves contact between the conjugate and the biomolecule, e.g., protein or nucleic acid, to be assayed. The in vivo applications are limited only by the means of detecting luminescence. In other words, the site of contact between the conjugate and the biomolecule to be assayed must be accessible by a luminescence detection means. In this regard, fiber optics can be used. Fiber optics enable light emission and detection as needed in the context of the present inventive methods.

EXAMPLES

The present invention is described further in the following examples. These examples serve to illustrate further the present invention and are not intended to limit the scope of the invention.

Example 1

This example demonstrates how to obtain a water-soluble luminescent quantum dot by attaching an attachment group, one end of which can bind to the cap of a luminescent quantum dot and the other end of which comprises a hydrophilic moiety.

Quantum dots comprising a CdSe core of 4.2 nm and a ZnS cap were prepared in accordance with the procedure developed by Hines and Guyot-Sionnest (*J. Phys. Chem.*, 100, 468–71 (1996)). The quantum dots were dissolved in chloroform and reacted with 1.0 M glacial mercapto-acetic acid for 2 hrs at room temperature with slow stirring. Subsequently,. an equal volume of aqueous PBS, pH 7.4, was added to the reaction mixture with vigorous shaking for 30 mins. Upon spontaneous separation of the chloroform and aqueous layers, the aqueous layer containing the mercapto-coated quantum dots was extracted. The aqueous layer was then centrifuged to pellet the mercapto-coated quantum dots and extracted at least four times to remove excess mercapto-acetic acid. The final pellet was resuspended in 10 ml of PBS, pH 7.4, and stored at room temperature until use. The mercapto-coated quantum dots remained soluble for at least one month.

Comparative Example 1a

This example demonstrates the preparation of a quantum dot which is not water-soluble.

Quantum dots having mercaptobenzoic acid groups on the surface thereof were constructed. Mercaptobenzoic acid was dissolved in a solution of 50% DMSO/50% methanol. The pH of the solution was adjusted to 11 by addition of tetramethyl ammonium hydroxide. The final concentration of mercaptobenzoic acid was 5 mM.

A 1 ml aliquot of the mercaptobenzoic acid solution was added to approximately 1 mg of the ZnS-capped quantum dots prepared as described in Example 1 and heated at 70° C. Although the mercaptobenzoic acid-bound quantum dots had temporarily solubilized, the mercaptobenzoic quantum dots began to aggregate rapidly after approximately one hour. Aggregation of quantum dots out of solution is an indication of instability. The mercaptobenzoic quantum dots were then purified using acetone and subsequently placed in PBS. Again, the quantum dots were unstable and precipitated out of solution after a few hours.

Example 2

This example demonstrates how to attach a proteinaceous biomolecule, such as a ligand, to an attachment group on the cap of a luminescent quantum dot by means of a crosslinking agent.

A 1 ml solution of the purified mercapto-quantum dots of Example 1 was reacted with 2 mg of transferring (Sigma Chemical Co., St. Louis, Mo.) and 1 mg of the crosslinking reagent EDAC (Sigma Chemical Co.) overnight at room temperature while vortexing. The solution was then centrifuged at 50,000 RPM for 1 hr to pellet the quantum dot-transferring bioconjugate and the supernatant was removed. This centrifugation step was repeated twice more. The purified transferring bioconjugates were dissolved in PBS (pH 7.4) and stored at room temperature.

Example 3

This example demonstrates how to attach a proteinaceous biomolecule, such as an antibody, to the attachment group on the cap of a luminescent quantum dot by means of a crosslinking agent.

A 1 ml solution of the purified mercapto-quantum dots of Example 1 was reacted with 2 mg of Immunoglobulin G (IgG) (Sigma Chemical Co.) and 1 mg of EDAC overnight at room temperature while vortexing. The solution was then centrifuged at 50,000 RPM for 1 hr to pellet the quantum dot-immunoglobulin bioconjugate and the supernatant was removed. This centrifugation step was repeated twice more.

The purified immunoglobulin bioconjugates were dissolved in PBS (pH 7.4) and stored at room temperature.

Example 4

This example demonstrates how to attach a nucleic acid to the attachment group on the cap of a luminescent quantum dot by means of a linker, such as a free amine group.

A 1 ml solution of the purified mercapto-quantum dots of Example 1 is reacted with 3'- or 5'-amine-modified oligonucleotides (Midland Certified Reagents, Midland, Tex.) and 1 mg of EDAC overnight at room temperature while vortexing. The solution is then centrifuged at 50,000 RPM for 1 hr to pellet the quantum dot-oligonucleotide bioconjugates and the supernatant is removed. This centrifugation step is repeated twice more. The purified oligonucleotide bioconjugates are dissolved in PBS (pH 7.4) and stored at room temperature. Using this approach, a direct linkage is formed between the carboxylic acid group on the quantum dot and an amine group on the nucleic acid.

Example 5

This example demonstrates how to attach a nucleic acid biomolecule to an attachment group on the cap of a luminescent quantum dot by means of a linker, such as streptavidin or neutravidin.

Streptavidin (Sigma Chemical Co.) is covalently linked to the mercapto-quantum dots according to the procedures given in Examples 2 and 3. After coating the quantum dots with streptavidin, biotinylated oligonucleotides (Midland Certified Reagents) are incubated with the streptavidin-coated quantum dots overnight at room temperature with vortexing. The quantum dot-streptavidin-biotinylated-oligonucleotides are purified by centrifugation at 50,000 RPM for 1 hr. The supernatant is discarded and the pellet is redissolved in PBS (pH 7.4). The centrifugation step is repeated twice more. The purified quantum dot-streptavidin-biotinylated-oligonucleotide is dissolved and stored in PBS. The same method can be used substituting neutravidin for streptavidin.

Example 6

This example demonstrates the method of using an antibody bioconjugate to detect an antibody in vitro, wherein the method is an immuno-agglutination assay.

A purified immunoglobulin bioconjugate comprising a water-soluble luminescent quantum dot attached to an immunoglobulin molecule, such as IgG, was prepared by the procedure given in Example 3. The luminescent quantum dot-immunoglobulin bioconjugate was reacted with 0.5 μg/ml of anti-Fab antibody, which binds to IgG molecules. The reaction mixture was allowed to incubate for one hour at room temperature. The anti-Fab antibody bound to the IgG molecules of the luminescent quantum dot-immunoglobulin bioconjugate, causing the luminescent bioconjugates to agglutinate. Agglutination was determined by detecting the luminescence with an epi-fluorescence microscope equipped with a high-resolution CCD camera (1.4 million pixels, Photometrix, Tuscon, Ariz.) and a 100 W mercury excitation lamp.

Example 7

This example demonstrates a method of using a protein bioconjugate to detect an antibody in vitro, wherein the method is an immuno-agglutination assay.

A purified protein bioconjugate comprising a water-soluble luminescent quantum dot and a proteinaceous biomolecule, such as an antigen, is prepared according to the procedure in Examples 2 and 3. A purified cell lysate is prepared from a blood sample by lysing the cells, centrifuging the sample to pellet the cellular debris, and then extracting the supernatant, which contains the purified cell lysate. The purified cell lysate is incubated with the luminescent quantum dot-antigen bioconjugate. If the antibody of interest is present in the cell lysate sample, it will recognize and bind to the antigen attached to the luminescent quantum dot-antigen conjugate, causing the luminescent quantum dots to agglutinate. Therefore, agglutination of the luminescent quantum dot conjugates indicates the presence of the antibody in the cell lysate sample. Agglutination is determined by luminescence according to the procedure given in Example 6. If desired, duplicate methods can be performed in order to compare the sample to a control. A suitable control includes the addition of the luminescent quantum dot-bioconjugate to a physiologically equivalent composition not comprising the target antibody.

Example 8

This example demonstrates a method of using an antibody bioconjugate, to detect a protein in vitro, wherein the method is an immuno-agglutination assay.

A purified antibody conjugate comprising a water-soluble luminescent quantum dot and an antibody is prepared according to the procedure in Example 3. A purified cell lysate is prepared from a blood or tissue sample according to the procedure given in Example 7. The purified cell lysate is incubated with the luminescent quantum dot-antibody conjugate. If the protein of interest is present in the cell lysate sample, the antibody molecule attached to the luminescent quantum dot-antibody conjugate will recognize and bind to the protein in the sample, causing the luminescent quantum dots to agglutinate. Agglutination, therefore, indicates the presence of the protein in the sample. The degree of agglutination will indicate the concentration of protein present in the cell lysate sample. The degree of agglutination is determined by luminescence according to the procedure given in Example 6. Of course, to estimate the concentration of protein in a sample, the luminescence of the quantum dot-conjugate-protein complex is compared to a series of standards comprising the luminescent quantum dot-bioconjugate of the present invention in contact with predetermined concentrations of target protein.

Example 9

This example demonstrates a method of using a protein bioconjugate to detect an antibody in vitro, wherein the method is a direct immunoassay.

A purified cell lysate is prepared from a blood sample according to the procedure given in Example 7. A purified protein bioconjugate comprising the water-soluble luminescent quantum dot and a proteinaceous biomolecule, such as an antigen, is prepared according to the procedure in Example 2. The chosen attached antigen is one which is specifically recognized by the antibody of interest. A sample of the purified cell lysate is pipetted onto a polystyrene surface and allowed to incubate for two hours at room temperature. The sample is removed and the polystyrene surface is washed with distilled water. To prevent non-specific binding, a 1% solution of Bovine Serum Albumin (BSA) (Sigma Chemical Co.) in PBS is pipetted onto the polystyrene surface and allowed to incubate for one hour at room temperature. After removing the BSA and washing the polystyrene surface with distilled water, the water-soluble luminescent quantum dot-antigen bioconjugate is pipetted onto the polystyrene surface and allowed to incubate. If the antibody of interest is present in the cell-lysate sample, it will recognize and bind to the antigen attached to the luminescent quantum dot-antigen bioconjugate. Luminescence of the quantum dot-antigen bioconjugate is detected by exciting the sample with an $Ar^+/Kr^-$ laser at 514 nm.

Example 10

This example demonstrates a method of using an antibody bioconjugate to detect a protein in vitro, wherein the method is a sandwich immunoassay.

A purified cell lysate is prepared from a blood or tissue sample according to the procedure given in Example 7. An antibody bioconjugate comprising the water-soluble luminescent quantum dot and an antibody is prepared according to the procedure given in Example 3. The chosen attached antibody is one which specifically recognizes the protein of interest. First, a "capturing" antibody which recognizes the protein of interest is pipetted onto a polystyrene surface and allowed to incubate for two hours at room temperature. The antibody is removed and the polystyrene surface is washed with distilled water. To prevent non-specific antibody binding, a 1% solution of BSA in PBS is pipetted onto the polystyrene surface and allowed to incubate for one hour at room temperature. After removing the BSA and washing the polystyrene surface with distilled water, the purified cell lysate is pipetted onto the polystyrene surface and allowed to incubate for two hours at room temperature. If the protein of interest is present in the cell-lysate sample, the "capturing" antibody will bind the protein. The polystyrene surface is washed with distilled water to remove unbound protein. Finally, the luminescent quantum dotantibody bioconjugate is added and allowed to incubate for two hours at room temperature. If the protein of interest is present, the antibody attached to the luminescent quantum dot-antibody bioconjugate will bind to it. Luminescence of the quantum dot-antibody bioconjugate is detected by exciting the sample with an $Ar^+/Kr^+$ laser at 514 nm.

Example 11

This example demonstrates a method of using a nucleic acid bioconjugate to detect a nucleic acid in vitro.

A purified mRNA sample is prepared from cells or tissue according to methods well-known in the art. The particular mRNA of interest will dictate which method and which cells or tissue will be used to isolate the MRNA. A nucleic acid bioconjugate comprising a water-soluble luminescent quantum dot and a nucleic acid is prepared according to the procedure given in Examples 4, 5, or 14. The attached nucleic acid is comprised of an oligonucleotide sequence which specifically hybridizes to the nucleic acid sequence of interest. An amine-modified polythymidine (Midland Certified Reagents) is covalently attached to a Biodyne C membrane (Pall Gelman Sciences, Ann Arbor, Mich.) by adding 100 µl of 0.1 µM amine-modified poly-thymidine, one strip of the Biodyne C membrane (0.5 cm×0.5 cm), and 1 mg of EDAC into a centrifuge tube and allowing the mixture to incubate overnight at room temperature. The next day, the Biodyne C membranes are rinsed with distilled water 3–4 times. The purified mRNA sample is added to the Biodyne C membrane to which the amine-modified poly-thymidine is attached and allowed to incubate for two hours at room temperature. The polyA tail of the mRNA molecules will hybridize with the attached poly-thymidine, allowing the mRNA to be attached to the Biodyne C membrane. The Biodyne C membrane is washed several times with distilled water to remove non-hybridized mRNA. Next, the oligonucleotide bioconjugate, comprising a water-soluble luminescent quantum dot and an oligonucleotide which specifically hybridizes to the mRNA of interest, is reacted with the Biodyne C membrane to which the amine-modified polythymidine and mRNA is attached and allowed to incubate overnight at room temperature. If the mRNA of interest is present, the luminescent quantum dot-oligonucleotide bioconjugate will hybridize to it. The Biodyne C membrane is washed several times with distilled water to remove excess non-hybridized luminescent quantum dot-oligonucleotide bioconjugates. Luminescence of the quantum dot-oligonucleotide bioconjugate is detected by exciting the sample with an $Ar^+/Kr^-$ laser at 514 nm.

Example 12

This example demonstrates a method of using a protein bioconjugate to detect receptor-mediated endocytosis in vivo.

A biomolecular conjugate comprising the water-soluble luminescent quantum dot and transferrin was prepared according to the procedure given in Example 2. HeLa cells were grown in minimum essential medium (MEM) containing 10% fetal calf serum, 1% penicillin/streptomycin, and fungizone. The cultured cells were incubated with the luminescent quantum dot-transferrin bioconjugates at 37° C. overnight. After repeated washing to remove excess bioconjugate, the cells were removed from the petri dish by trypsinization and placed on a glass coverslip for imaging with an epi-fluorescence microscope equipped with a high-resolution CCD camera (1.4 million pixels, Photometrix) and a 100 W mercury excitation lamp as described in Example 6. Luminescence inside of the HeLa cells indicated that the transferrin of the conjugate was still biologically active and was recognized by transferrin receptors on the HeLa cell surfaces. HeLa cells incubated with the water-soluble luminescent quantum dots of Example 1 were not luminescent. Measurement of the amount of internal luminescence over time enables the determination of the rate of endocytosis.

Example 13

This example demonstrates how to attach a proteinaceous biomolecule, such as a ligand, to an attachment group on the cap of a luminescent quantum dot by means of a linker, such as streptavidin or neutravidin.

Streptavidin (Sigma Chemical Co.) is covalently linked to the mercaptoquantum dots according to the procedures given in Example 2. A protein, such as transferrin, is attached to biotin using the EDAC cross-linking method. The attachment to biotin must occur at an amino acid which can be derivatized with little change in protein activity. A solution of purified streptavidin-coated quantum dots is reacted with the biotinylated transferrin overnight at room temperature while vortexing. The biotinylated transferrin and streptavidin-coated quantum dots can be reacted in a specific molar ratio, such as 1:1, 1:2, etc., so as produce the desired number of protein molecules per quantum dot. The solution is then centrifuged at 50,000 RPM for 1 hr to pellet the quantum dot-transferrin bioconjugate and the supernatant is removed. This centrifugation step is repeated twice more. The purified transferrin bioconjugates are dissolved in PBS (pH 7.4) and stored at room temperature.

Example 14

This example demonstrates how to attach a nucleic acid to the attachment group on the cap of a luminescent quantum dot by means of a linker, such as a thiol group.

Quantum dots comprising a CdSe core of 4.2 nm and a ZnS cap are prepared in accordance with the procedure developed by Hines and Guyot-Sionnest (1996), supra. Thiol-modified oligonucleotides are purchased or prepared using standard synthesis procedures. A 1 ml solution of CdSe(ZnS) quantum dots is reacted with thiol-modified oligonucleotides. The ZnS coat of the quantum dot contains unreacted Zn molecules to which the thiol group of the modified oligonucleotide can bind. The solution is then centrifuged at 50,000 RPM for 1 hr to pellet the quantum dot-oligonucleotide bioconjugates and the supernatant is removed. This centrifugation step is repeated twice more. The purified oligonucleotide bioconjugates are dissolved in PBS (pH 7.4) and stored at room temperature.

Example 15

This example demonstrates a method of making a specially designed nucleic acid bioconjugate which further contains a quencher to detect a nucleic acid in vitro.

The specially designed nucleic acid bioconjugate comprises a single-stranded oligonucleotide having a stem-and-loop structure, a quantum dot moiety, and a quenching moiety. The oligonucleotide is modified to have a primary amine group at the 3' end, which amine-modified oligonucleotide is available from Midland Certified Reagents. Using standard cross-linking procedures, the oligonucleotide is further modified to have a biotin group at the 5' end. A nonfluorescent organic chromophore, 4-[4'-dimethylaminophenylazo] benzoic acid (DABCYL), is covalently linked to the 3' amino group by using an amino-reactive derivative DABCYL (available from Molecular Probes, Eugene, Oreg.). Quantum dots are first derivatized with strepavidin according to the methods described in Example 2 and then conjugated to the 5' biotin group at a 1:1 molar ratio. The oligonucleotide bioconjugate is purified using gel-filtration columns and HPLC.

Example 16

This example demonstrates how to obtain a water-soluble luminescent quantum dot by attaching a mercaptosuccinic attachment group to the cap of a luminescent quantum dot. This example further demonstrates how to attach a nucleic acid to the mercaptosuccinic attachment group by means of a linker, such as a free thiol group.

Quantum dots comprising a CdSe core of 4.2 nm and a ZnS cap were prepared as described previously. The quantum dots were dissolved in mercaptosuccinic acid (0.5 g/ml, pH 9.0) and allowed to mix for 15–30 mins at room temperature. A series of acetone precipitations at a concentration of 30% acetone/70% quantum dot were preformed to purify sufficiently the hydrophilic luminescent quantum dot. The resulting mercaptosuccinic acid-quantum dots were suspended in 15 mM EDAC solution at pH 6.0.

A 1 ml solution of the purified mercaptosuccinic-coated luminescent quantum dots was reacted with either 3'- or 5'-thiol-terminated, 15-mer oligonucleotides (Midland Certified Reagents) at a relative concentration of approximately 100 oligonucleotides per quantum dot. The reaction was allowed to proceed for 30–60 mins while mixing. The luminescent quantum dot-DNA conjugates were purified several times by acetone precipitation (30% acetone/70% conjugate). The luminescent quantum dot-DNA conjugates were subsequently stored in a hybridization buffer (0.4 M NaCl, pH 7.0).

Example 17

This example demonstrates a method of using a nucleic acid bioconjugate to detect a nucleic acid in vitro.

Figure 4:
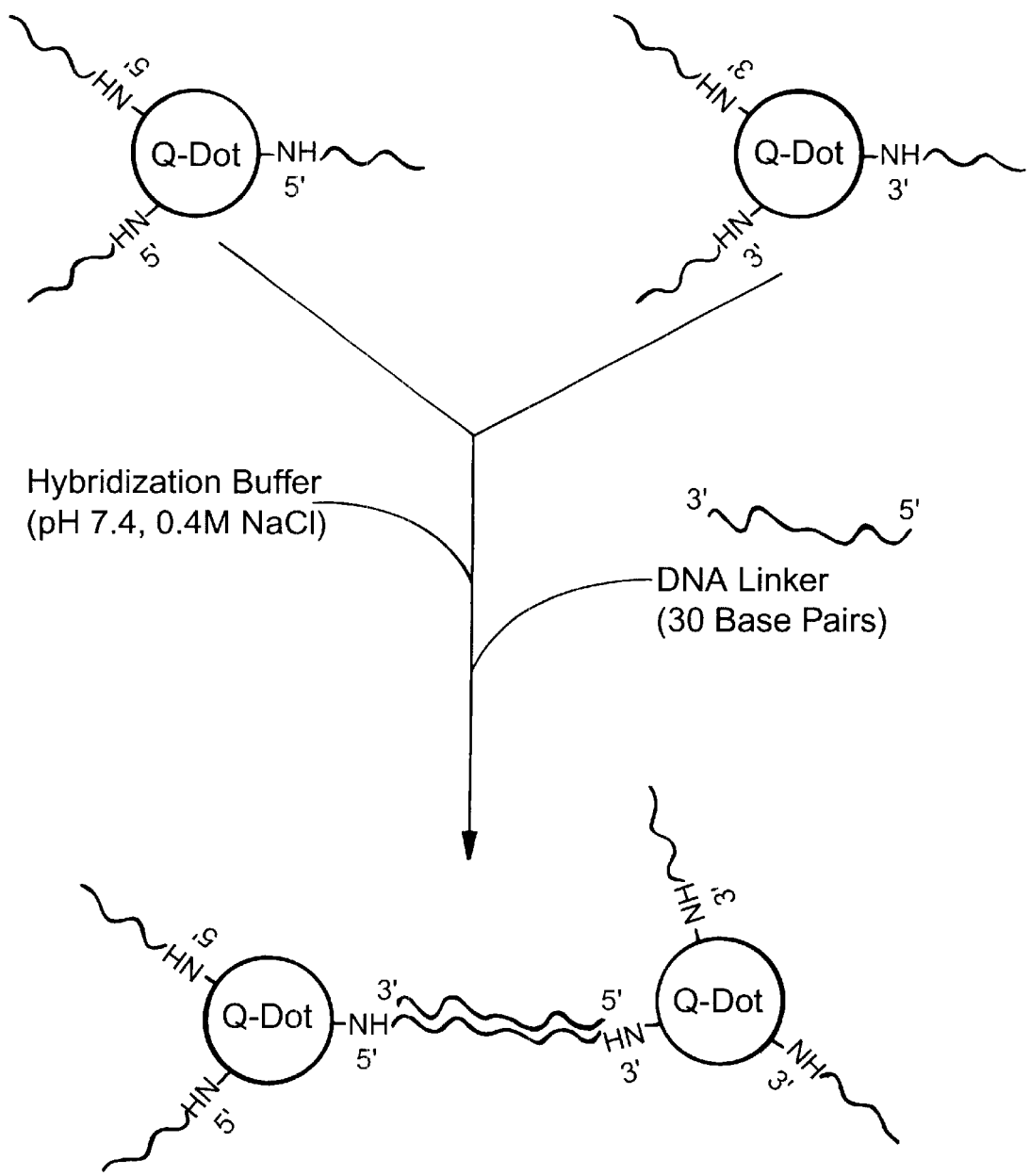
FIG. 4 is a schematic diagram of bioconjugates comprising a luminescent semiconductor quantum dot and an oligonucleotide and the bioconjugates bound by a DNA linker.

Equal aliquots of the 3'- and 5'-thiol-terminated oligonucleotide-luminescent quantum dot conjugates produced as described in Example 16 were suspended in a hybridization buffer (0.4 NaCl, pH 7.0). A complementary 30-mer linker was added to the hybridization buffer at a relative concentration of about one linker for every two luminescent quantum dot conjugates. The 30-mer linker was specifically designed to hybridize with the thiol-terminated 15-mer oligonucleotides of the luminescent quantum dot conjugates. Therefore, if the oligonucleotides of the luminescent quantum dot conjugates retained their biological activity, two quantum dots would hybridize to the linker oligonucleotide and subsequently aggregate as demonstrated in FIG. 4. Hybridization was monitored for 1–12 hours and aggregation of the bioconjugates was observed. Aggregation was imaged using an inverted wide-field Hg lamp excitation and sensitive CCD detection.

All of the references cited herein, including patents, patent applications and publications, are hereby incorporated in their entireties by reference.

While this invention has been described with an emphasis upon preferred embodiments, it will be apparent to those of ordinary skill in the art that variations in the preferred embodiments can be prepared and used and that the invention can be practiced otherwise than as specifically described herein. The present invention is intended to include such variations and alternative practices. Accordingly, this invention includes all modifications encompassed within the spirit and scope of the invention as defined by the following claims.

What is claimed is:

1. A water-soluble luminescent semiconductor quantum dot, which comprises a core, a cap and a hydrophilic attachment group, wherein said hydrophilic attachment group is an organic group comprising a sulfur atom and at least one hydrophilic substituent selected from the group consisting of a sulfonic acid or salt thereof, a sulfamic acid or salt thereof, a quaternary ammonium salt, and a hydroxy, wherein the water-soluble luminescent semiconductor quantum dot remains in solution for at least one day.

2. The water-soluble luminescent semiconductor quantum dot of claim 1, wherein the hydrophilic attachment group is attached to said quantum dot via the sulfur atom.

3. The water-soluble luminescent semiconductor quantum dot of claim 1, wherein said organic group is a $C_1$–$C_6$ alkyl group or an aryl group.

4. The water-soluble luminescent semiconductor quantum dot of claim 1, wherein said organic group is a $C_1$–$C_6$ alkyl group.

5. The water-soluble luminescent semiconductor quantum dot of claim 1, wherein said hydrophilic attachment group is a thiol alcohol.

6. The water-soluble luminescent semiconductor quantum dot of claim 1, wherein the core of the quantum dot is selected from the group consisting of IIB–VIB semiconductors, IIIB–VB semiconductors, and IVB–IVB semiconductors and the size of the core is from about 1 nm to about 10 nm.

7. The water-soluble luminescent semiconductor quantum dot of claim 6, wherein the core of the quantum dot is selected from the group consisting of IIB–VIB semiconductors and the size of the core is from about 2 nm to about 5 nm.

8. The water-soluble luminescent semiconductor quantum dot of claim 7, wherein the core of the quantum dot is CdS or CdSe.

9. The water-soluble luminescent semiconductor quantum dot of claim 8, wherein the core of the quantum dot is CdSe.

10. The water-soluble luminescent semiconductor quantum dot of claim 8, wherein the cap is ZnS.

11. The water-soluble luminescent semiconductor quantum dot of claim 9, wherein the size of the core is about 4.2 nm.

12. The water-soluble luminescent semiconductor quantum dot of claim 1, wherein the cap is selected from the group consisting of IIB–VIB semiconductors of high band gap.

13. The water-soluble luminescent semiconductor quantum dot of claim 12, wherein the cap is ZnS.

14. The water-soluble luminescent semiconductor quantum dot of claim 12, wherein the cap is CdS.

15. The water-soluble luminescent quantum dot of claim 9, wherein the cap is CdS.

16. A composition comprising the water-soluble luminescent semiconductor quantum dot of claim 1 and an aqueous carrier.

* * * * *

UNITED STATES PATENT AND TRADEMARK OFFICE
CERTIFICATE OF CORRECTION

PATENT NO.     : 6,468,808 B1
DATED          : October 22, 2002
INVENTOR(S)    : Nie et al.

It is certified that error appears in the above-identified patent and that said Letters Patent is hereby corrected as shown below:

<u>Title page,</u>
Please insert reference no. -- WO 90/15666 -- under "FOREIGN PATENT DOCUMENTS".

<u>Column 11,</u>
Line 27, "thereof The" should read -- thereof. The --.

<u>Column 17,</u>
Line 7, "$Ar^+/Kr^-$" should read -- $Ar^+/Kr^+$ --.

<u>Column 18,</u>
Line 14, "$Ar^+/Kr^-$" should read -- $Ar^+/Kr^+$ --.

Signed and Sealed this

Tenth Day of June, 2003

JAMES E. ROGAN
*Director of the United States Patent and Trademark Office*